(12) United States Patent
Otsubo (10) Patent No.: US 7,192,422 B2
(45) Date of Patent: Mar. 20, 2007

(54) PULL-ON DISPOSABLE WEARING ARTICLE

(75) Inventor: Toshifumi Otsubo, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 108 days.

(21) Appl. No.: 10/870,940

(22) Filed: Jun. 21, 2004

(65) Prior Publication Data

US 2004/0260264 A1    Dec. 23, 2004

(30) Foreign Application Priority Data

Jun. 23, 2003    (JP) ............................. 2003-178527

(51) Int. Cl.
*A61F 13/15* (2006.01)

(52) U.S. Cl. .......................... 604/385.28; 604/385.27; 604/385.201

(58) Field of Classification Search .......... 604/385.28, 604/396, 385.27, 385.201, 385.24, 385.25
See application file for complete search history.

(56) References Cited

U.S. PATENT DOCUMENTS

| | | | | |
|---|---|---|---|---|
| 3,710,797 | A * | 1/1973 | Marsan ................ | 604/385.201 |
| 3,744,494 | A * | 7/1973 | Marsan ...................... | 604/378 |
| 3,807,402 | A * | 4/1974 | Miller et al. ................ | 604/378 |
| 3,860,004 | A * | 1/1975 | Nystrand .................... | 604/365 |
| 3,968,799 | A * | 7/1976 | Schrading ................... | 604/365 |
| 4,808,177 | A * | 2/1989 | DesMarais et al. .... | 604/385.27 |
| 4,822,435 | A * | 4/1989 | Igaue et al. ................. | 156/164 |
| 4,897,084 | A * | 1/1990 | Ternstrom et al. ..... | 604/385.27 |
| 5,246,431 | A * | 9/1993 | Minetola et al. ....... | 604/385.28 |
| 5,401,275 | A * | 3/1995 | Flug et al. ................ | 604/391 |
| H1630 | H * | 1/1997 | Roe et al. ................ | 604/385.28 |
| 5,601,546 | A * | 2/1997 | Tanji et al. ............ | 604/385.28 |
| 5,672,166 | A * | 9/1997 | Vandemoortele ....... | 604/385.28 |
| 5,746,730 | A * | 5/1998 | Suzuki et al. .......... | 604/385.26 |
| 6,165,160 | A * | 12/2000 | Suzuki et al. ......... | 604/385.201 |
| 6,293,934 | B1 * | 9/2001 | Kumasaka ............. | 604/385.27 |
| 6,383,170 | B1 * | 5/2002 | Mishima et al. ....... | 604/385.19 |
| 6,616,646 | B2 * | 9/2003 | Wada et al. .......... | 604/385.101 |
| 6,652,504 | B1 * | 11/2003 | Olson et al. ........... | 604/385.25 |
| 6,666,851 | B2 * | 12/2003 | Otsubo et al. ........ | 604/385.201 |
| 6,955,667 | B1 * | 10/2005 | Tanaka et al. ......... | 604/385.24 |
| 7,001,368 | B2 * | 2/2006 | Otsubo .................... | 604/385.3 |
| 7,028,841 | B2 * | 4/2006 | Otsubo ........................ | 206/494 |
| 2002/0029028 | A1 * | 3/2002 | Shimada et al. ....... | 604/385.28 |
| 2005/0004544 | A1 * | 1/2005 | Otsubo et al. ......... | 604/385.01 |

(Continued)

FOREIGN PATENT DOCUMENTS

JP    2003-10244    1/2003

(Continued)

*Primary Examiner*—Tatyana Zalukaeva
*Assistant Examiner*—Paula L. Craig
(74) *Attorney, Agent, or Firm*—Lowe Hauptman & Berner LLP (57) ABSTRACT

A disposable wearing article has first and second barrier flaps on first and second side flaps, respectively. A crotch region is formed with first and second folding guide lines diverging from the vicinity of proximal edges of the first and second barrier flaps toward side edges of the first and second side flaps, respectively. First and second sections of the crotch region are tucked inwardly along the first and second folding guide lines in a transverse direction of the article, respectively, but distal portions of the first and second barrier flaps are not tucked inwardly of the article.

10 Claims, 11 Drawing Sheets

U.S. PATENT DOCUMENTS

2005/0004548 A1* 1/2005 Otsubo et al. ......... 604/385.25
2005/0075618 A1* 4/2005 Kenmochi et al. ..... 604/385.27

FOREIGN PATENT DOCUMENTS

| WO | WO 2002/096333 A2 * | 12/2002 |
|---|---|---|
| WO | WO 2004/019846 A1 * | 3/2003 |
| WO | WO 2003/063747 A1 * | 8/2003 |
| WO | WO 2003/079950 A1 * | 10/2003 |

* cited by examiner

PULL-ON DISPOSABLE WEARING ARTICLE

RELATED APPLICATIONS

The present application is based on, and claims priority from, Japanese Application Serial Number 2003-178527, filed Jun. 23, 2003, the disclosure of which is hereby incorporated by reference herein in its entirety.

BACKGROUND OF THE INVENTION

The present invention relates to a pull-on disposable wearing article used for absorption and containment of urine and other bodily exudates.

A pull-on disposable wearing article is known in the art. The article has a waist-hole, a pair of leg-holes, a front waist region, a rear waist region and a crotch region extending between these waist regions. The crotch region is folded inward in a transverse direction along folding guide lines (See Japanese Laid-Open Patent Application No. 2003-10244, hereinafter referred to as Citation).

The article disclosed in Citation comprises a body fluid absorbing zone extending between the front and rear waist regions and having a liquid-absorbent core therein, a pair of end flaps extending in the transverse direction outside longitudinally opposite ends of the absorbing zone and a pair of barrier flaps extending outside transversely opposite side edges. The side flaps extending in the front and rear waist regions are overlapped and permanently bonded together in the vicinity of side edges of these side flaps along a plurality of welding lines arranged intermittently in the longitudinal direction.

Each of the barrier flaps comprises a proximal portion, a pair of longitudinally opposite ends lying on the respective end flaps and collapsed inwardly in the transverse direction and a distal portion extending in the longitudinal direction between the ends. The distal portion is provided with a stretchable elastic member contractibly attached thereto and thereby normally biased to rise up along its proximal edge above the side flap.

The crotch region is formed with a pair of folding guide lines each diverging in a V-shape from a point on a transverse center line of the crotch region toward the respective side flaps. A generally triangular section defined between each of the V-shaped folding guide lines and the associated side edge of the side flap is tucked inward in the transverse direction of the article along these folding guide lines. By tucking these generally triangular sections of the crotch region, a transverse dimension of the body fluid absorbing zone in the crotch region can be reduced to ensure that the absorbing zone can be neatly received in a crotch region of the wearer.

In the case of the article disclosed in Citation, the distal portions of the respective barrier flaps overlying a part of the crotch region are tucked inwardly in the transverse direction of the article together with this part of the crotch region so that each of these distal portions is curved inwardly in the transverse direction of the article substantially in a V-shape. However, zones of the distal portions extending in adjacency to the proximal portions segments may remain collapsed toward the absorbing zone. As a result, it can not be expected for these zones to function as barriers against body fluid and, in the worst case, body fluid may leak out beyond the barrier flaps. In addition, a distance between apices of the barrier flaps is inevitably reduced as the barrier flaps are curved inward in the transverse direction of the article. This may cause also body fluid to leak out beyond the barrier flaps.

Furthermore, the zones of the movable segments being collapsed may partially cover the absorbing zone and unacceptably restrain a desired absorbing function.

SUMMARY OF THE INVENTION

In view of the problem as has been described above, it is an object of the present invention to provide a pull-on disposable wearing article improved so that an absorbing zone may be neatly received in a crotch region of the wearer and distal portions of respective barrier flaps lying in a crotch region of the article may sufficiently function as barriers against bodily exudates without an anxiety that the distal portions might restrain a desired absorbing function of the absorbing zone.

The object set forth above is achieved, according to the present invention, by a pull-on disposable wearing article comprising: a front waist region; a rear waist region opposed to the front waist region; a crotch region extending between these waist regions; a waist-hole; a pair of leg-holes; an absorbing zone extending between the front and rear waist regions; a pair of end flaps extending in a transverse direction outside longitudinally opposite ends of the absorbing zone; first and second side flaps extending in a longitudinal direction outside transversely opposite side edges of the absorbing zone; a first barrier flap extending in the longitudinal direction on a side of the first side flap and a second barrier flap extending in the longitudinal direction on a side of the second side flap, each of these first and second barrier flaps comprising a proximal portion extending in the longitudinal direction, longitudinally opposite ends lying on the end flaps and collapsed in one of in- and outwardly in the transverse direction and a distal portion being elastically stretchable and contractible and extending between the longitudinally opposite ends, and the distal portions of the first and second barrier flaps being normally biased to rise up on proximal edges thereof extending in the vicinities of the side edges of the absorbing zone above the absorbing zone so as to form barriers against bodily exudates.

The article further comprises: the crotch region being formed in a longitudinally middle zone thereof with a first folding guide line diverging from a vicinity of the proximal edge of the first barrier flap toward a side edge of the first side flap in the transverse direction and a second folding guide line diverging from a vicinity of the proximal edge of the second barrier flap toward a side edge of the second side flap in the transverse direction and, in the crotch region, a first section defined by the first folding guide line and the side edge of the first side flap is tucked inwardly along the first folding guide line in the transverse direction of the article and a second section defined by the second folding guide line and the side edge of the second side flap is tucked inwardly along the second folding guide line while the distal portions of the first and second barrier flaps extend almost linearly in the longitudinal direction without being tucked inwardly in the transverse direction of the article.

The invention includes the following preferred embodiments.

Stretchable elastic members extending in the longitudinal direction are contractibly attached to the distal portions of the first and second barrier flaps.

The article further comprises a third barrier flap extending in the longitudinal direction outside the first barrier flap and a fourth barrier flap extending in the longitudinal direction outside the second side flap, each of the third and fourth barrier flaps comprising a proximal portion extending in the longitudinal direction, longitudinally opposite ends lying on the end flaps and collapsed in one of in- and outwardly in the transverse direction and a distal portion being elastically stretchable and contractible and extending between the longitudinally opposite fixed ends, the distal portions of the third and fourth barrier flaps being normally biased to rise up on proximal edges thereof lying in the first and second side flaps above these side flaps and, in the crotch region, the distal portions of the third and fourth barrier f laps being tucked inwardly together with the first and second sections along the first and second folding guide lines in the transverse direction of the article.

Stretchable elastic members extending in the longitudinal direction are contractibly attached to the distal portions of the third and fourth barrier flaps.

The article comprises a liquid-pervious topsheet facing the wearer's skin, a liquid-impervious backsheet facing away from the wearer's skin and a liquid-absorbent core interposed between these sheets wherein the core is laid in the absorbing zone.

The pull-on disposable wearing article according to the present invention provides various advantages as follow: There is no anxiety that the distal portions of the first and second barrier flaps in entirety might be collapsed toward the absorbing zone while the first and second sections of the crotch region are tucked inwardly. This is because that these distal portions are not tucked inwardly but remain substantially linear. The distal portions of the first and second barrier flaps in entirety rise up on the respective proximal edges above the absorbing zone and function as the barriers against bodily exudates. Thus bodily exudates can be reliably prevented from flowing beyond the distal portions and consequently leaking sideways in the crotch region even when bodily exudates spread in the absorbing zone in the transverse direction. The distance between the distal edges of the first and second barrier flaps is not reduced as the article is put on the wearer's body and therefore there is no anxiety that bodily exudates might be discharged outside the barrier flaps. The distal portions of the first and second barrier flaps do not cover the absorbing zone and it is unlikely that the absorbing function desired for the absorbing zone might be restrained by the distal portions.

In the case of the article exploited so that the third and fourth barrier flaps overlie the first and second barrier flaps, the distal portions of the third and fourth barrier flaps extending in the first and second sections of the crotch region are tucked inwardly together with the first and second sections in the transverse direction. The zones of the distal portions of the third and fourth barrier flaps folded in this manner come in contact with the distal portions of the first and second barrier flaps from outside so as to support the distal portions of the first and second barrier flaps. In this way, the distal portions of the first and second barrier flaps are reliably prevented from being collapsed outwardly in the transverse direction of the article.

DETAILED DESCRIPTION OF THE PREFERRED EMBODIMENTS

Details of pull-on disposable wearing article according to the present invention will be more fully understood from the description given hereunder with reference to the accompanying drawings.

Figure 1:
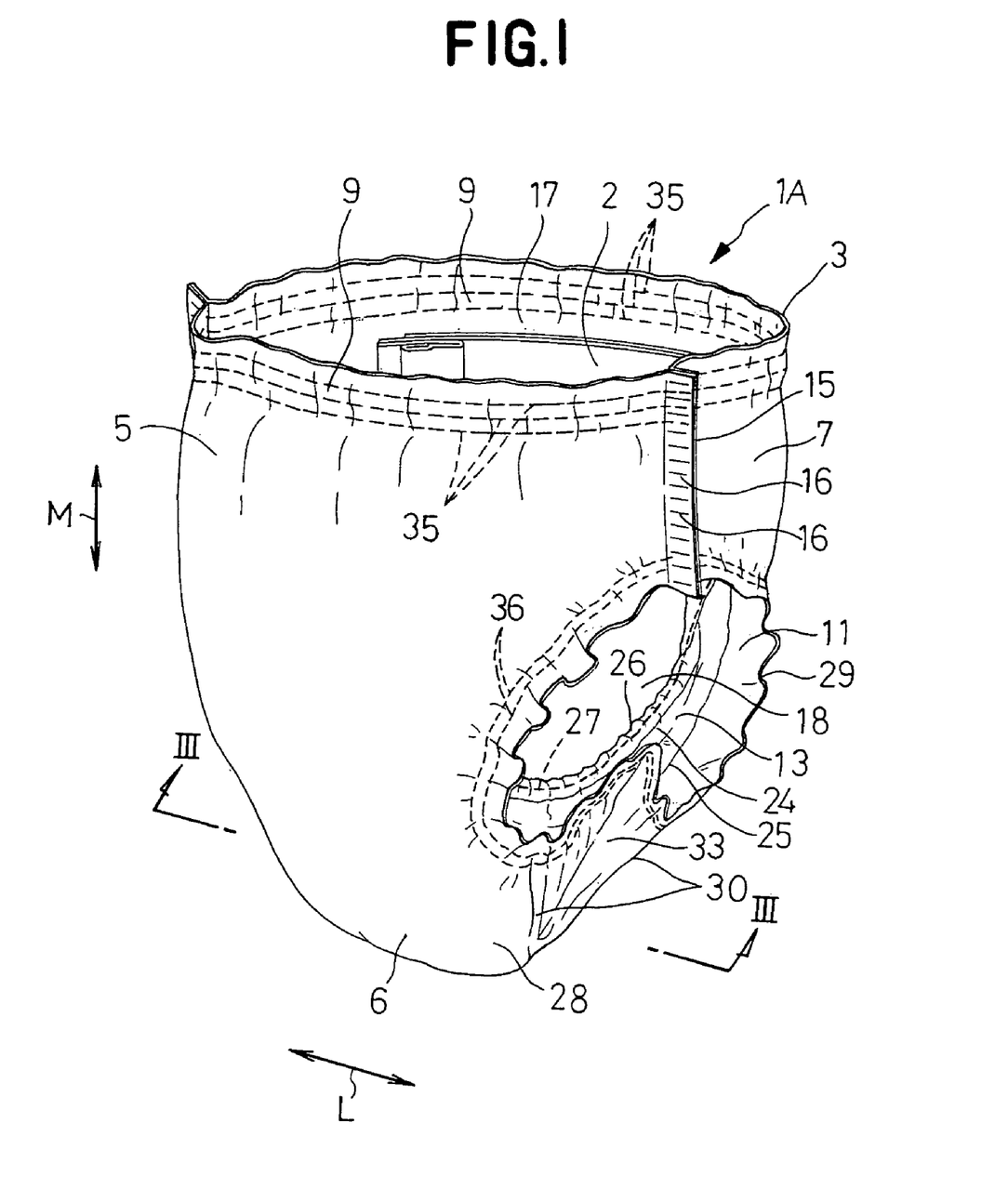
FIG. 1 is a perspective view showing an example of the wearing article according to the invention.
Figure 2:
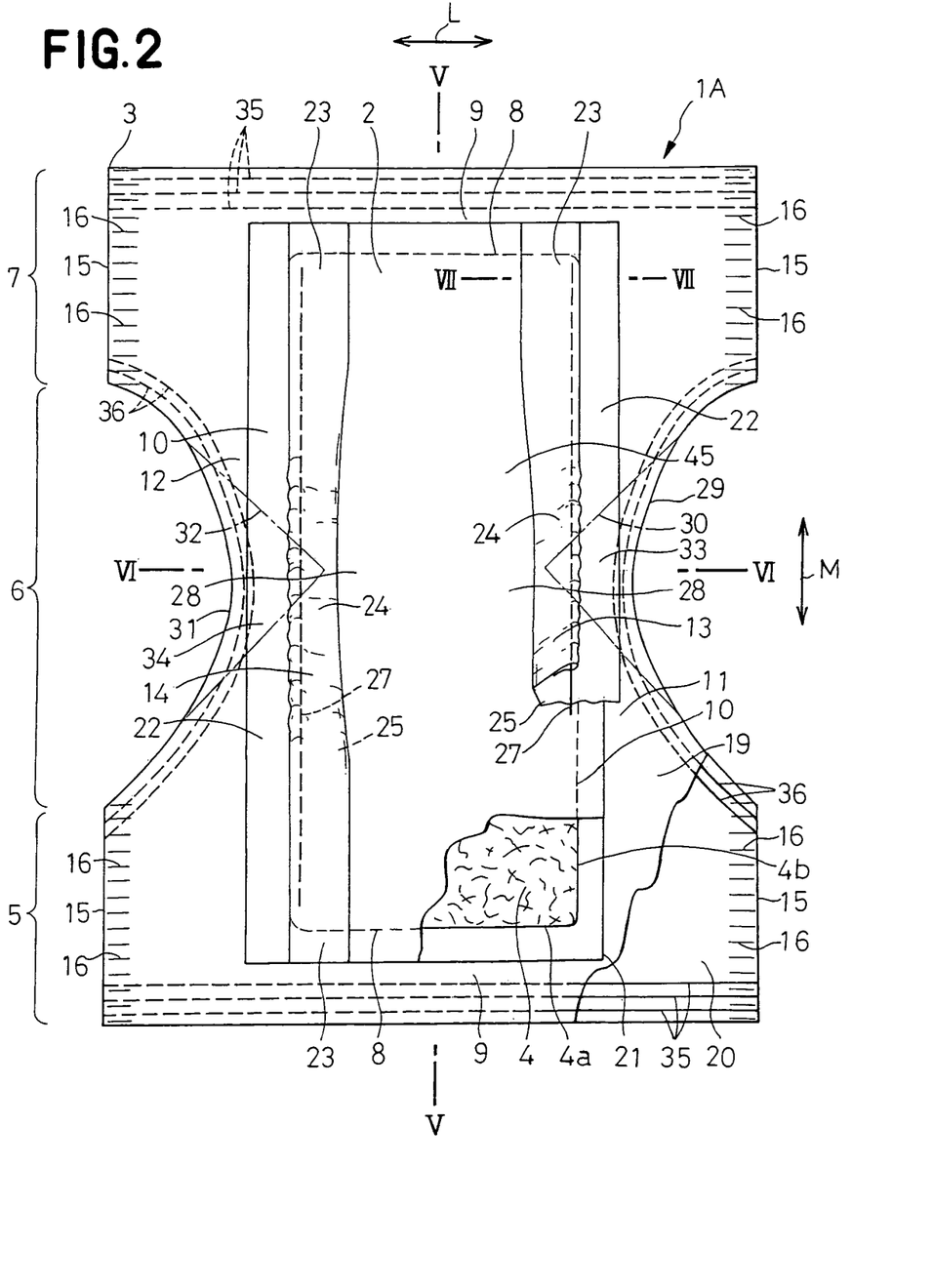
FIG. 2 is a partially cutaway, developed plan view showing the article of FIG. 1 with its front and rear waist regions disconnected along its side flaps disconnected.
Figure 3:
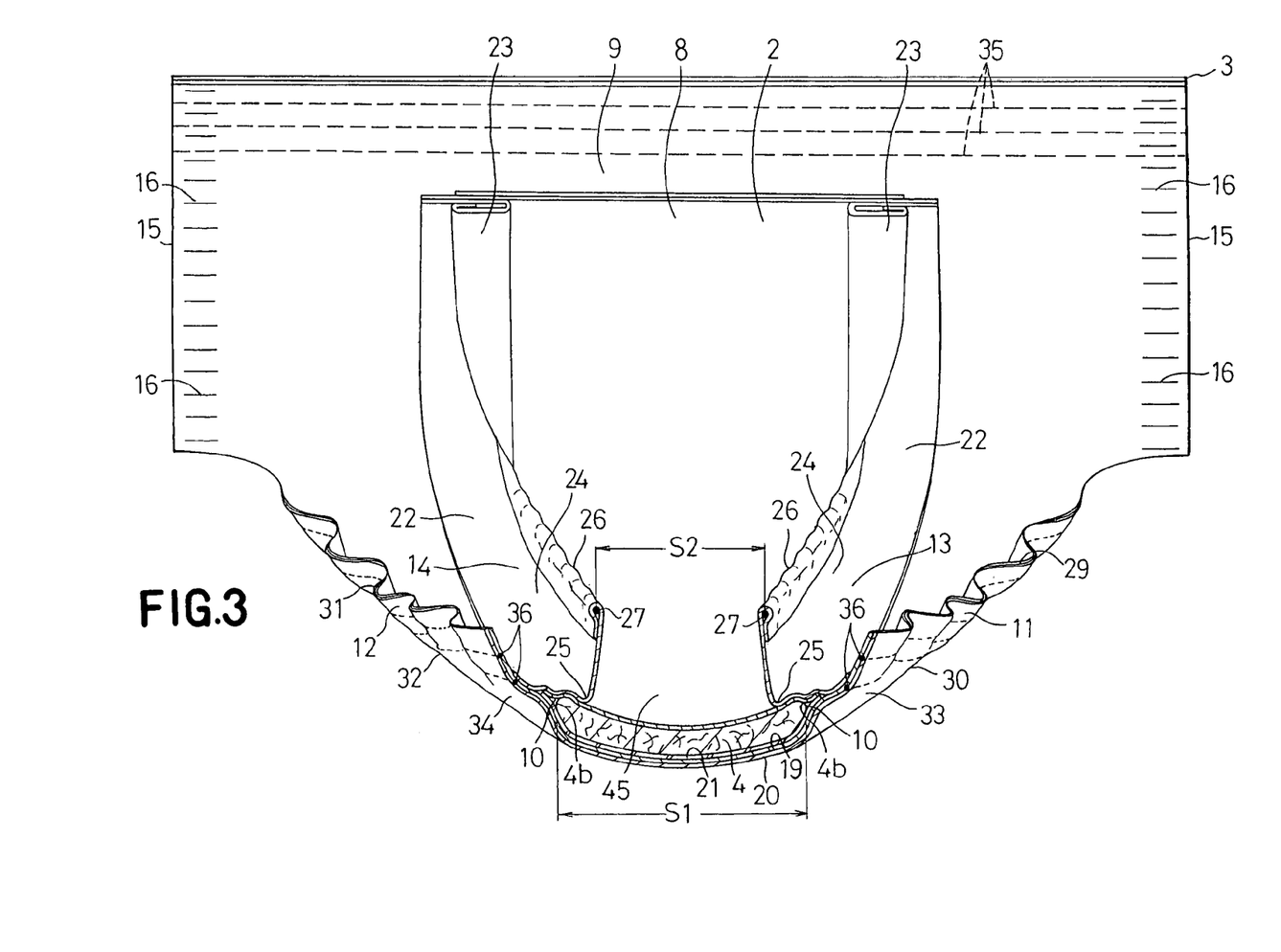
FIG. 3 is a sectional view taken along the line III—III in FIG. 1.
Figure 4:
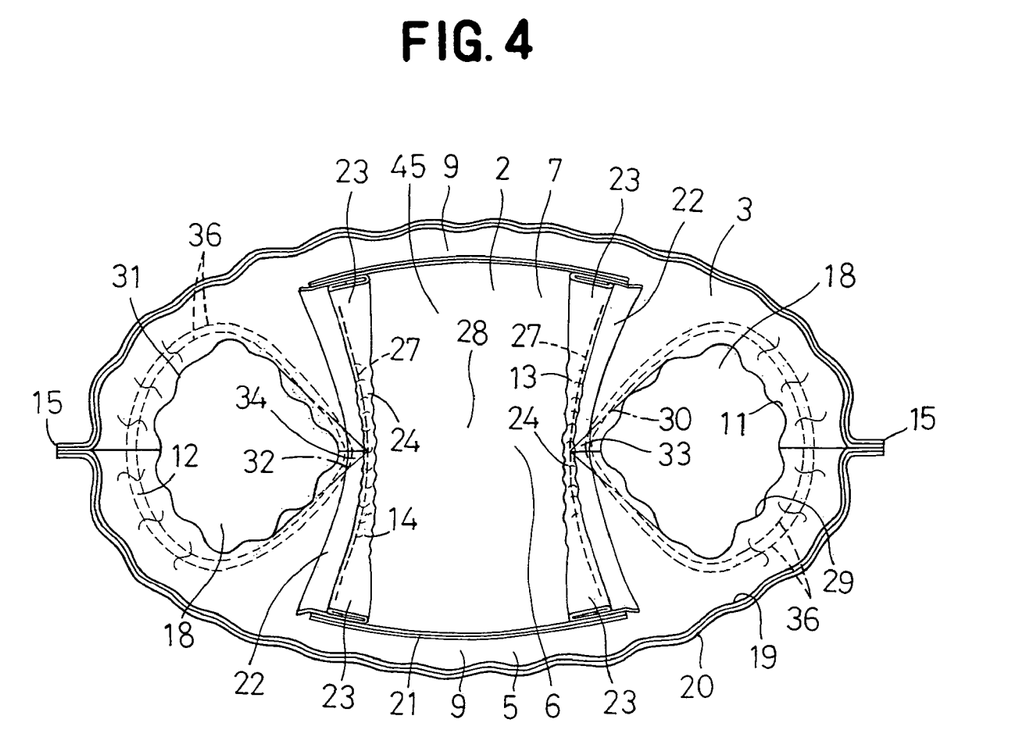
FIG. 4 is a perspective view showing the article of FIG. 1 with its waist hole as viewed from above the waist-hole.

FIGS. 1 to 7 shows a wearing article 1A according to an embodiment of the invention. In FIGS. 1 and 2, a transverse direction is indicated by an arrow L and a longitudinal direction is indicated by an arrow M.

Referring now to FIGS. 1 to 4, the article 1A comprises the liquid-pervious topsheet 2, the liquid-impervious backsheet 3 and the liquid-absorbent core 4 interposed between the top- and backsheets 2, 3. The article 1A defines a front waist region 5, a rear waist region 7 opposed to the front waist region 5 and a crotch region 6 extending between these waist regions 5, 7.

The article 1A has an absorbing zone 45 in which a desired function of the core 4 is effective for absorption and containment of bodily exudates, a pair of end flaps 9 extending in the transverse direction outside longitudinally opposite ends 8 (corresponding to longitudinally opposite ends 4a of the core 4) of the absorbing zone 45, first and second side flaps 11, 12 respectively extending in the longitudinal direction outside transversely opposite side edges 10 (corresponding to transversely opposite side edges 4b) of the absorbing zone 45, a first barrier flap 13 extending in the longitudinal direction on the side of the first side flap 11 and a second barrier flap 14 extending in the longitudinal direction on the side of the second side flap 12. The absorbing zone 45 extends between the front and rear waist regions 5, 7.

In the crotch region 6, the side flaps 11, 12 describe circular arcs which are convex inwardly in the transverse direction of the diaper 1A. The article 1A thus has a generally hourglass-like planar shape in its developed state. Portions of the respective side flaps 11, 12 extending in the front and rear waist regions 5, 7 are overlapped and permanently bonded together in vicinities of side edges thereof along a plurality of welding lines 16 arranged intermittently in the longitudinal direction, and thereby a waist-hole 17 and a pair of leg-holes 18 are formed, respectively.

The topsheet 2 is formed from a hydrophilic fibrous nonwoven fabric. The backsheet 3 is formed from a composite sheet comprising a pair of breathable liquid-resistant sheet 19, 20 such as hydrophobic fibrous nonwoven fabric layers being substantially identical in size as well as in shape and rectangular breathable liquid-impervious sheet 21 such as plastic film 21 having an area smaller than those of breathable liquid-resistant sheets 19, 20. These sheets 19, 20, 21 have respective surfaces thereof opposed one to another permanently bonded one to another by means of suitable adhesives.

The core 4 has a generally rectangular shape which is relatively long in the longitudinal direction and laid in the absorbing zone 45. The core 4 is contoured by the longitudinally opposite ends 4a extending in the transverse direction to define the longitudinally opposite ends 8 of the absorbing zone 45 and the transversely opposite side edges 4b extending in the longitudinal direction to define the transversely opposite side edges 10 of the absorbing zone 45. The core 4 is permanently bonded to the inner surface of the topsheet 2 and to the inner surface of the backsheet 3 (i.e., to the inner surface of the film 21) by means of suitable adhesives.

The core 4 comprises a mixture of particulate or fibrous super-absorbent polymers and fluff pulp fibers or a mixture of particulate or fibrous super-absorbent polymers, fluff pulp fibers and thermoplastic synthetic resin fibers, in any case, compressed to a desired thickness. Thus, the core 4 has a stiffness higher than those of the top- and backsheets 2, 3. Preferably, the core 4 is entirely wrapped with a liquid-pervious sheet such as a tissue paper or hydrophilic fibrous nonwoven fabric in order to prevent the core 4 from getting out its initial shape and/or to prevent the polymers from falling off. The polymers may be selected from the group consisting of a starch-based polymer, a cellulose-based polymer and a synthetic polymer.

Each of the first and second barrier flaps 13, 14 comprises a proximal portion 22 extending in the longitudinal direction between the front and rear waist regions 5, 7, longitudinally opposite ends 23 lying on the respective end flaps 9 and collapsed outwardly in the transverse direction of the article 1A and a distal portion 24 extending in the longitudinal direction between these longitudinal opposite ends 23. The distal portion 24 has a proximal edge 25 extending immediately outside the side edge 10 of the absorbing zone 45 (in the vicinity of the side edge 4b of the core 4) and along which the distal portion 24 rise and a distal edge 26 opposed to the proximal edge 25 (See FIG. 3). A stretchable elastic member 27 extending in the longitudinal direction is contractibly attached to the distal portion 24 in the vicinity of its distal edge 26. The elastic member 27 is permanently bonded to the distal portion 24 so that the elastic member 27 is wrapped by a part of the distal portion 24. The distal portion 24 rises up along the proximal edge 25 above the absorbing zone 45 and thereby forms a barrier against bodily exudates as the elastic member 27 contracts in the longitudinal direction.

As will be seen in FIG. 2, the crotch region 6 is formed in its longitudinal middle zone 28 with a first folding guide line 30 extending in the transverse direction so as to diverge from the vicinity of the proximal edge 25 of the first barrier flap 13 to a side edge 29 of the side flap 11 and a second folding guide line 32 extending in the transverse direction so as to diverge from the vicinity of the proximal edge 25 of the second barrier flap 14 to a side edge 31 of the second side flap 12. More specifically, the first folding guide line 30 diverges from the vicinity of the proximal edge 25 of the first barrier flap 13 toward the first side flap 11 to describe a generally V-shape and the second folding guide line 32 diverges from the vicinity of the proximal edge 25 of the second barrier flap 14 toward the first side flap 12 to describe a generally V-shape. As used here the term "vicinity of the proximal edge 25" means, in addition to the proximal edge 25, a location slightly shifted from the proximal edge 25 toward the side flap 11, 12 and a location slightly shifted inwardly from the proximal edge 25 in the transverse direction of the absorbing zone 45.

The crotch region 6 is formed with a generally triangular first section 33 defined between the first folding guide line 30 and the side edge 29 of the first side flap 11 and a generally triangular section 34 defined between the second folding guide line 32 and the side edge 31 of the second side flap 12. The first section 33 is tucked inwardly along the first folding guide line 30 in the transverse direction of the article 1A and the second section 34 is tucked inwardly along the second folding guide line 32 in the transverse direction of the article 1A. The distal portions 24 of the first and second barrier flaps 13, 14 lying in the longitudinally middle zone 28 of the crotch region 6 are not tucked inwardly in the transverse direction of the article 1A, as will be apparent from FIG. 4. Therefore, the distal portions 24 are not bent inwardly in the transverse direction of the article 1A but extend in the longitudinal direction so as to describe generally straight lines, respectively. In other words, the distal portions 24 are not bent inwardly in the transverse direction of the article 1A but extend so as to describe generally U-shapes.

The vicinity of the side edges 4b of the core 4 as well as the proximal portions 22 of the barrier flaps 13, 14 all extending in the first and second sections 33, 34 are tucked inwardly along the first and second folding guide lines 30, 32 together with the first and second sections 33, 34 in the transverse direction of the article 1A.

The minimum transverse dimension S1 between the transversely opposite side edges 10 of the absorbing zone 45 in the longitudinally middle zone 28 of the crotch region 6 is preferably in a range of about 4 to 9 cm and the minimum distance S2 between the distal edges 26 of the respective distal portions 24 in the longitudinally middle zone 28 in the crotch region 6 is preferably in a range of about 3 to 8 cm. If the transverse dimension S1 exceeds about 9 cm, it will be impossible for the absorbing zone 45 to be neatly received in the crotch region of the wearer as the article 1A is put on the wearer's body and the core 4 laid in the absorbing zone 45 may enhance a bulkiness of the absorbing zone 45 due to a relatively high stiffness of the core 4, causing the wearer to experience a feeling of discomfort. In addition to such inconvenience, the absorbing zone 45 will be formed with a plurality of irregular creases as the crotch region 6 is squeezed in the wearer's crotch region and these creases will necessarily deteriorate bodily exudates absorbing function of the absorbing zone 45. If the minimum distance S2 is less than about 3 cm, on the other hand, the distance between the distal edges 26 of the respective distal portions 24 will be smaller than a transverse dimension of the wearer's crotch region, leading to a possibility that bodily exudates might be properly discharged on the absorbing zone 45 which should be exposed between the distal edges 26 of the respective distal portions 24 and bodily exudates might be discharged at least partially on the outer sides the barrier flaps 13, 14.

To obtain the article 1A shown in FIG. 1 from its developed state as shown in FIG. 2, the article 1A may be folded in two about the crotch region 6 with the topsheet 2 inside so that the front and rear waist regions 5, 7 face each other, then the side flaps 11, 2 in the front and rear waist region may permanently bonded to each other in the vicinity of the side edges 15 thereof. Now the first section 33 of the crotch region 6 may be tucked inwardly along the first folding guide line 30 in the transverse direction of the article 1A and the second section 34 of the crotch region 6 may be tucked inwardly along the second folding guide line 32 in the transverse direction of the article 1A.

A plurality of waist elastic members 35 extending in the transverse direction are contractibly attached to each of the end flaps 9. These waist elastic members 35 are interposed between the sheets 19, 20 constituting the backsheet 3 and permanently bonded to the respective surfaces of these sheets 19, 20 opposed to each other. The longitudinally opposite ends 23 of the respective barrier flaps 13, 14 lying on the respective end flaps 9 are permanently bonded to the proximal portions 22 extending in the vicinity of the side edges 10 of the absorbing zone 45 (See FIG. 7). Alternatively, the longitudinally opposite fixed ends 23 of the respective barrier flaps 13, 14 lying on the respective end flaps 9 may be permanently bonded to the outer surface of the topsheet 2 in the vicinity of the side edges 10 of the absorbing zone 45 with these ends 23 collapsed inward in the transverse direction of the article 1A.

Figure 5:
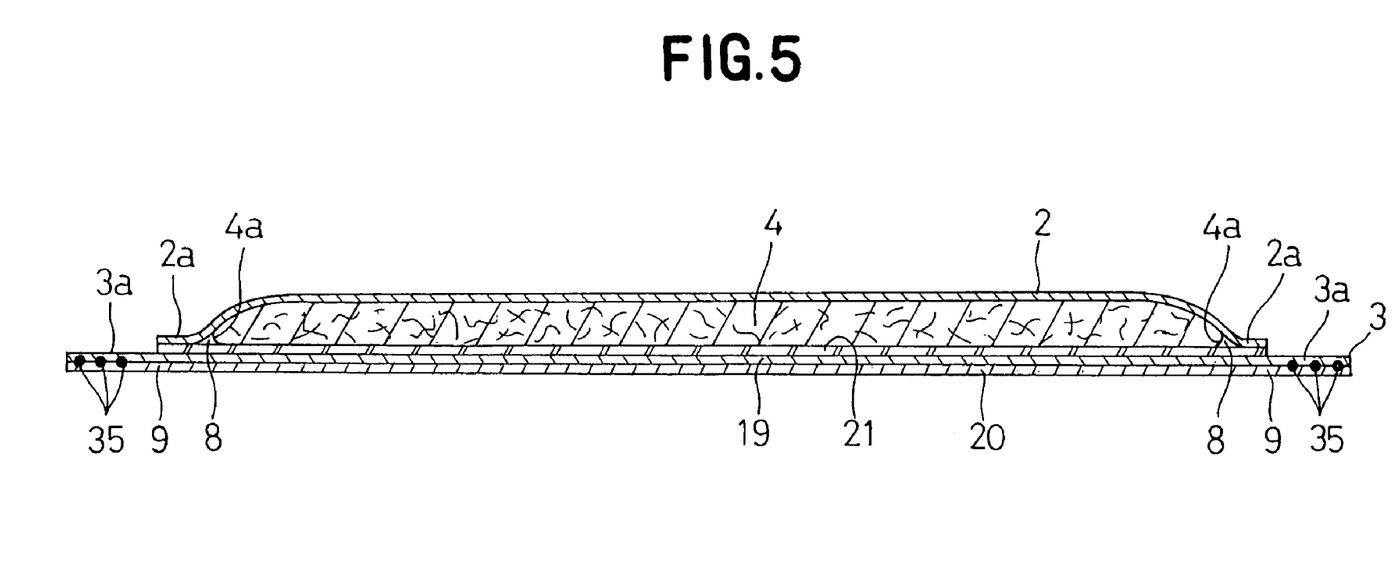
FIG. 5 is a sectional view taken along the line V—V in FIG. 2.
Figure 6:
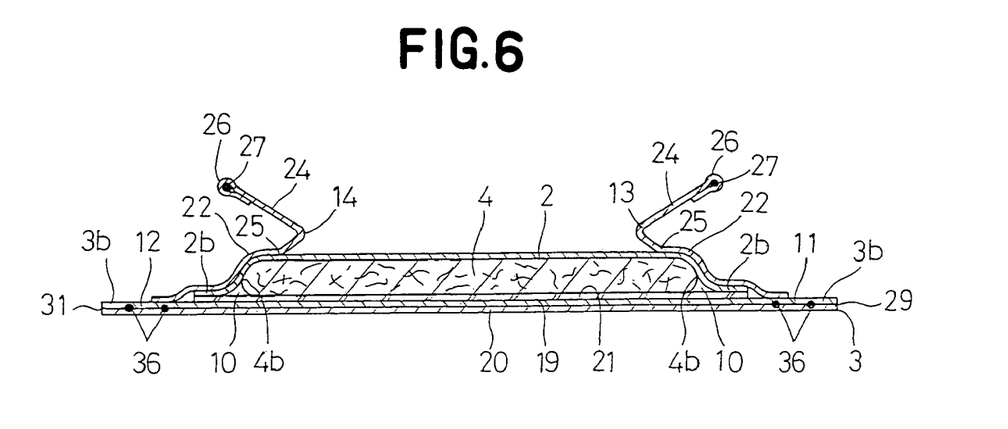
FIG. 6 is a sectional view taken along the line VI—VI in FIG. 2.
Figure 7:
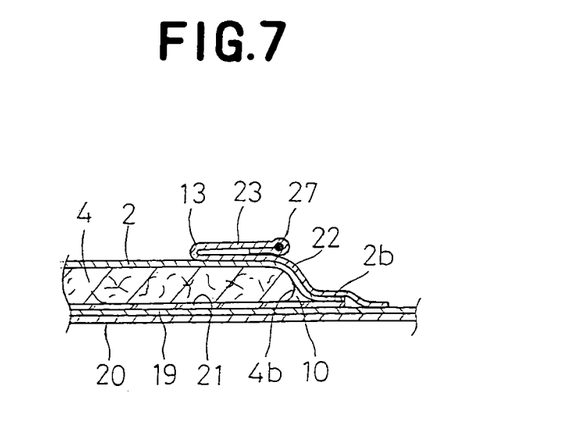
FIG. 7 is a sectional view taken along the line VII—VII in FIG. 2.

Referring to FIGS. 5 to 7 each of the end flaps 9 has most of its portion formed from the backsheet 3. In the end flaps 9, the longitudinally opposite ends 2a of the topsheet 2 extend in the longitudinal direction slightly beyond the longitudinally opposite ends 4a of the core 4 and the longitudinally opposite ends 3a of the backsheet 3 extend in the longitudinal direction beyond the ends 2a of the topsheet 2. The sheet 21 constituting the backsheet 3 extends in the longitudinal direction beyond the ends 4a of the core 4 by a dimension generally equal to the dimension by which the ends 2a of the topsheet 2 extend beyond the ends 4a of the core 4.

The side flaps 11, 12 principally comprise the backsheet 3 and the barrier flaps 13, 14. In the side flaps 11, 12, the side edges 2b of the topsheet 2 extend outwardly slightly beyond the side edges 4b of the core 4 in the transverse direction and the side edges 3b of the backsheet 3 as well as the proximal portions 22 of the respective barrier flaps 13, 14 extend outwardly beyond the side edges 2b of the topsheet 2. The sheet 21 constituting the backsheet 3 extends outward beyond the side edges 4b of the core 4 by a dimension generally equal to the dimension by which the side edges 2b of the topsheet 2 extend outwardly beyond the side edges 4b of the core 4.

In the side flaps 11, 12, the side edges 2b, 3b of the top- and backsheets 2, 3, respectively, and the proximal portions 22 of the barrier flaps 13, 14 are overlapped together wherein the proximal portions 22 of the flaps 13, 14 are permanently bonded to the respective outer surfaces of the top- and backsheets 2, 3 along the side edges 2b, 3b thereof and the inner surface of the topsheet 2 is permanently bonded to the inner surface of the backsheet 3 (specifically to the inner surface of the sheet 21) along the side edges 2b, 3b thereof.

Leg elastic members 36 extending in the longitudinal direction are contractibly attached to the side flaps 11, 12. These leg elastic members 36 are interposed between the sheets 19, 20 constituting the backsheet 3 and permanently bonded to the respective surfaces of these sheets opposed to each other.

The first and second sections 33, 34 of the crotch region 6 are tucked inwardly along the first and second folding guide lines 30, 32, respectively, and thereby the transverse dimension of the crotch region 6 in its longitudinal middle zone 28 can be reduced. Thus the absorbing zone 45 of the crotch region 6 is neatly received in the wearer's crotch region as the article 1A is put on the wearer's body and it is unlikely that the core 4 laid in the absorbing zone 45 might enhance the bulkiness of this zone 45 and the article 1A might give the wearer a feeling of discomfort due to the enhanced stiffness. Even when the crotch region 6 is squeezed in the wearer's crotch region, there is unlikely that the absorbing zone 45 might be formed with a plurality of irregular creases and the absorbing function of the zone 45 might be thereby deteriorated.

While the first and second sections 33, 34 of the crotch region 6 are tucked inwardly, the distal portions 24 of the first and second barrier flaps 13, 14 extend almost linearly without being affected by such tucking. There is no anxiety, therefore, that the distal portions 24 might be collapsed toward the absorbing zone 45 as the article of prior art has conventionally been the case. In the case of the diaper 1A, the distal portions 24 of the barrier flaps 13, 14 rise up in entirety above the absorbing zone 45 and thereby effectively function as the barriers against bodily exudates so that, even if body exudates spread in the absorbing zone 45 in the transverse direction, it is unlikely that bodily exudates might flow beyond the distal portions 24 and thereby any sideway leakage of bodily exudates in the crotch region 6 can be reliably prevented.

The article 1A is free from an anxiety that the distal edges 26 of the distal portions 24 of the respective barrier flaps 13, 14 might get nearer to each other as the article 1A is put on the wearer's body and consequently bodily exudates might be discharged on outer sides of the barrier flaps 24. Furthermore, it is unlikely that the distal portions 24 might cover the absorbing zone 45 and the absorbing function desired for the absorbing zone 45 might be restrained by the distal portions 24. Thus bodily exudates discharged on the article 1A put on the wearer's body can be reliably absorbed by the core 4 through the topsheet 2 and contained therein.

FIGS. 8 to 13 shows a wearing article 1B according to another embodiment of the invention, where components, portions and zones similar to those previously described are denoted by the same reference numeral and the detailed description thereof is omitted to avoid the repetition.

In FIGS. 8 to 13, the article has a third barrier flap 37 extending in the longitudinal direction on the side of the first side flap 11 and a fourth barrier flap 38 extending in the longitudinal direction on the side of the second flap 12, in addition to the first and second barrier flaps 13, 14.

The third barrier flap 37 overlies the first side flap 11 outside the first barrier flap 13 and is contiguous to the first barrier flap 13. The fourth barrier flap 38 overlies the second side flap 12 outside the second barrier flap 14 and is contiguous to the second barrier flap 14.

Each of the third and fourth barrier flaps 37, 38 comprises a proximal portion 39 extending in the longitudinal direction between the front and rear waist regions 5, 7, longitudinally opposite ends 40 lying on the respective end flaps 9 and collapsed outwardly in the transverse direction of the article 1B and a distal portion 41 extending in the longitudinal direction between these longitudinal opposite ends 40. The distal portion 41 has a proximal edge 42 and a distal edge 43 opposed to the proximal edge 42 both lying on the side flap 11, 12 (See FIG. 10). A stretchable elastic member 44 extending in the longitudinal direction is contractibly attached to the distal portion 41 along the distal edge 43. The distal portion 41 of the third and fourth barrier flaps 37, 38 are normally biased to rise up on the respective proximal edges 42 above the side flaps 11, 12.

The crotch region 6 is formed with a generally triangular first section 33 defined between the first folding guide line 30 and the side edge 29 of the first side flap 11 and a generally triangular section 34 defined between the second folding guide line 32 and the side edge 31 of the second side flap 12. In the crotch region 6, the first section 33 is tucked inwardly along the first folding guide line 30 in the transverse direction of the article 1B and the second section 34 is tucked inwardly along the second folding guide line 32 in the transverse direction of the article 1B. The distal portion 41 of the third and fourth barrier flaps 37, 38 extending in the first and second sections 33, 34 are tucked inwardly together with the first and second sections 33, 34 along the first and second folding guide lines 30, 32 in the transverse direction of the article 1B and bent inwardly so as to describe generally V-shapes, respectively, in the transverse direction of the article 1B.

Figure 10:
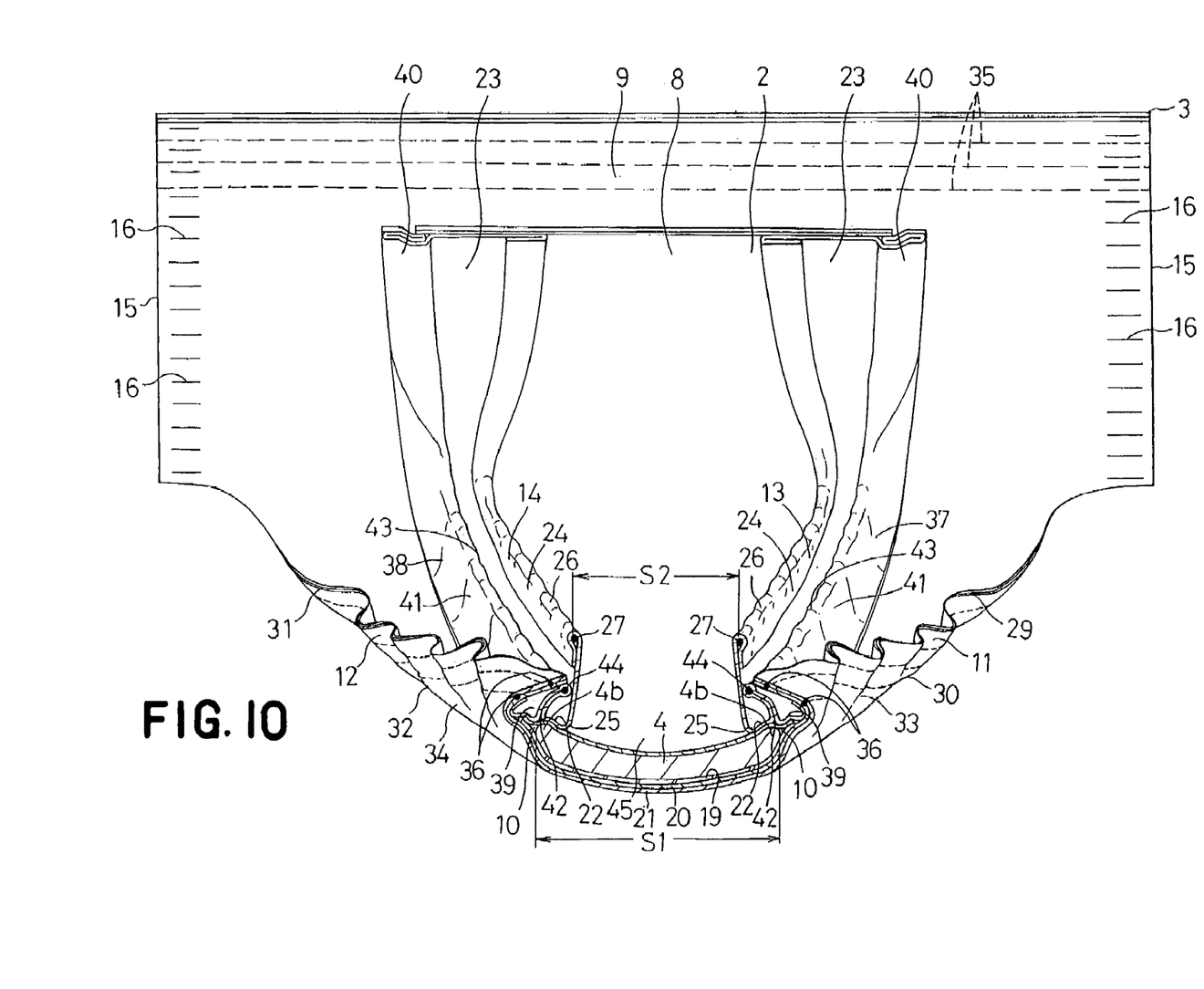
FIG. 10 is a sectional view taken along the line X—X in FIG. 8.
Figure 11:
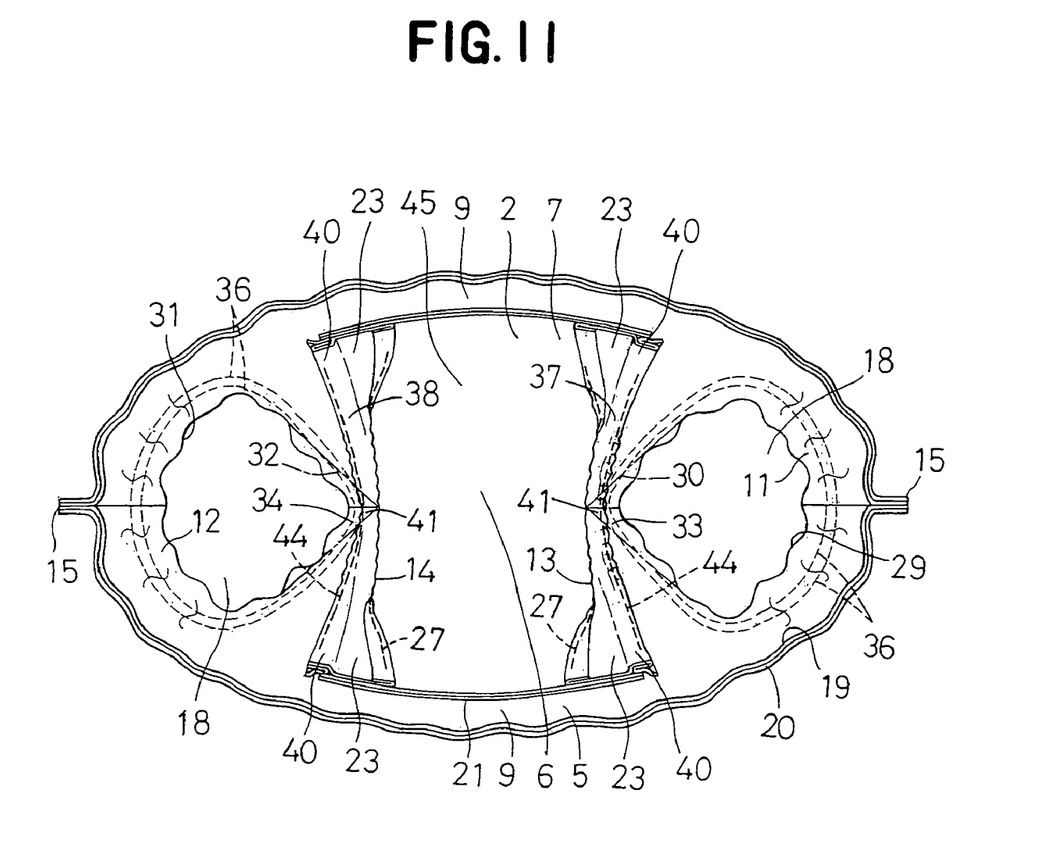
FIG. 11 is a perspective view showing the article of FIG. 8 with its waist hole as viewed from above the waist-hole.

In the longitudinally middle zone 28 of the crotch region 6, the distal portions 24 of the first and second barrier flaps 13, 14 lying in this zone 28 are not tucked inwardly in the transverse direction of the article 1B, as will be apparent from FIG. 11. Therefore, the distal portions 24 are not bent inwardly in the transverse direction of the article 1B but extend in the longitudinal direction so as to describe generally straight lines, respectively. The vicinity of the side edges 4b of the core 4 lying in the first and second section 33, 34 as well as the proximal portions 22, 39 of the barrier flaps 13, 14, 37, 38 are tucked inwardly together with the first and second sections 33, 34 along the first and second folding guide lines 30, 32, respectively, in the transverse direction of the. article 1B. In the crotch region 6, folded zones of the distal portions 41 of the third and fourth barrier flaps 37, 38 are in contact with the distal portions 24 of the first and second barrier flaps 13, 14 (See FIG. 10).

Figure 8:
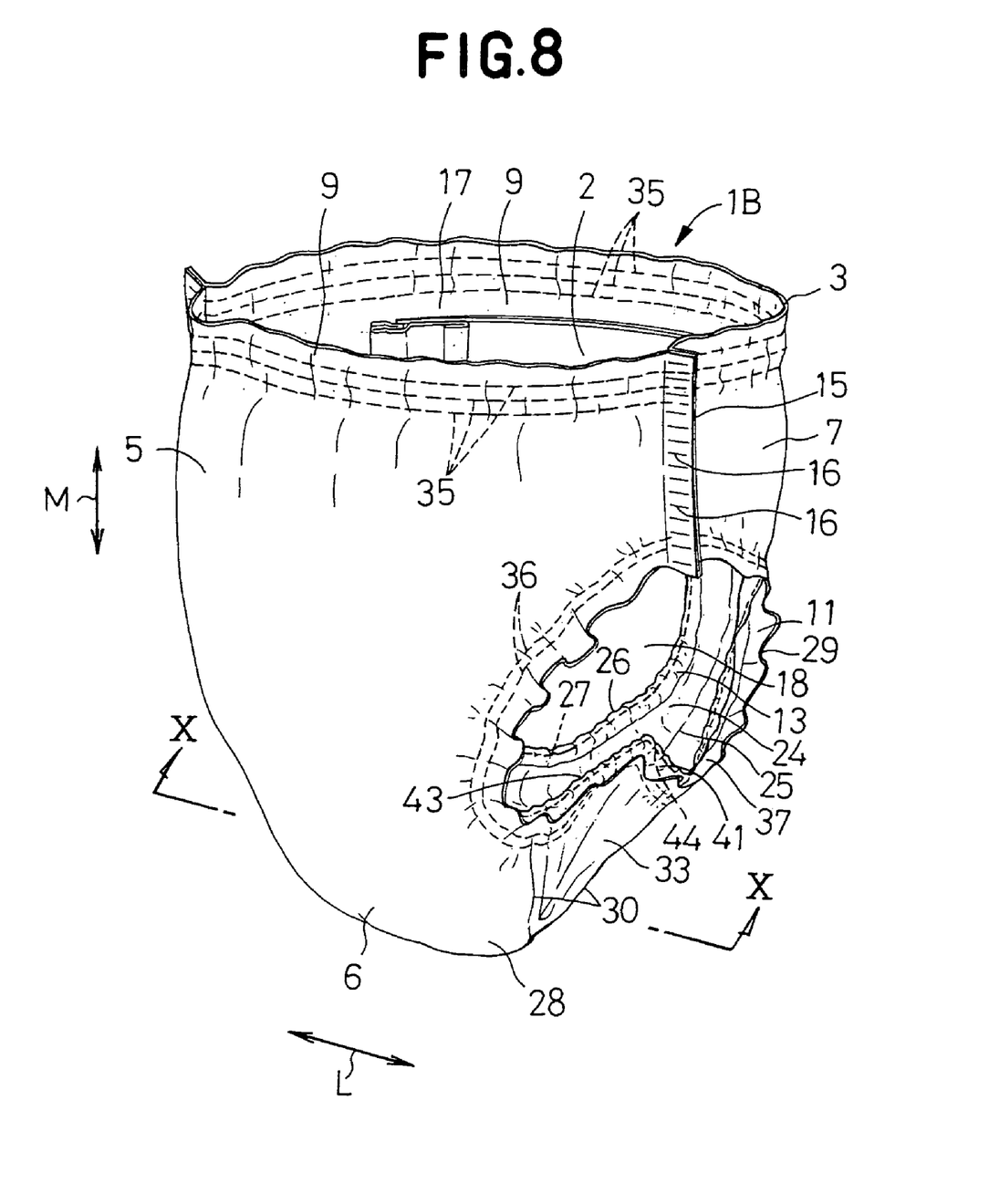
FIG. 8 is a perspective view showing another example of the wearing article according to the invention.
Figure 9:
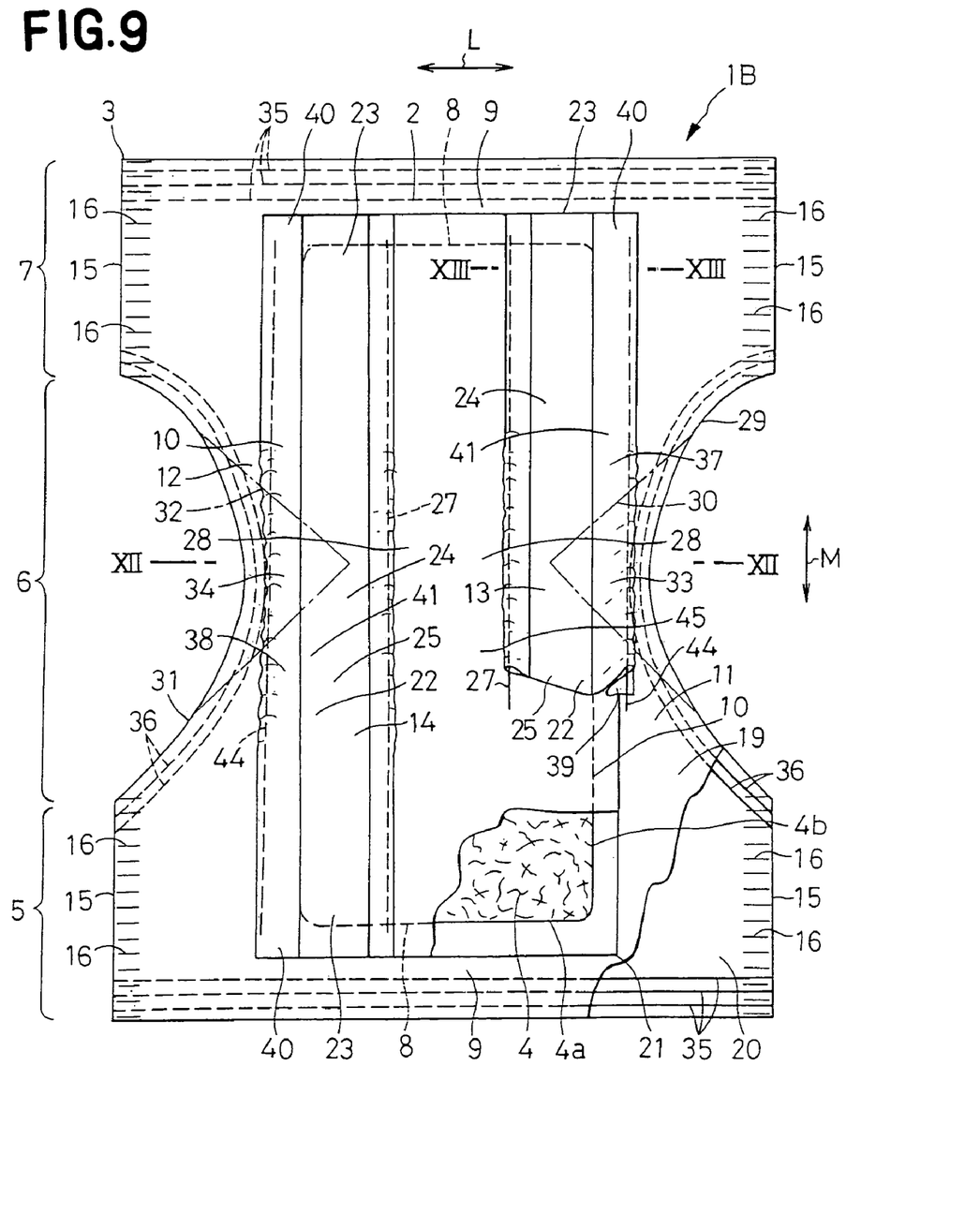
FIG. 9 is a partially cutaway, developed plan view showing the article of FIG. 8 with its front and rear waist regions disconnected along its side flaps disconnected.

In the longitudinally middle zone 28 of the crotch region 6, the minimum transverse dimension S1 between the transversely opposite side edges 10 of the absorbing zone 45 and the minimum distance S2 between the distal edges 26 of the respective distal portions 24 of the first and second barrier flaps 13, 14 are the same as those in the article 1A shown in FIG. 1. The sequence in which the article 1B of FIG. 8 is obtained from its developed state shown in FIG. 10 is the same as the sequence having been described in reference with FIG. 3.

Figure 12:
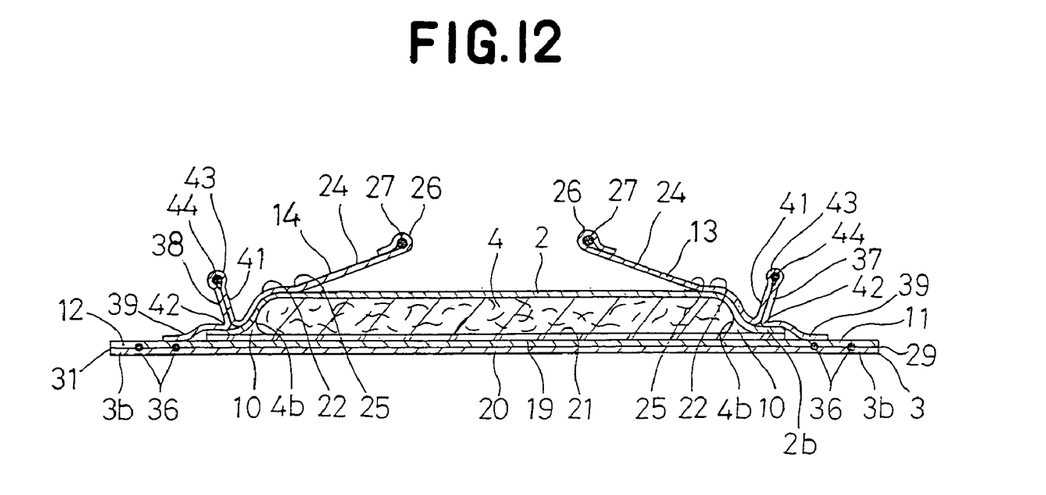
FIG. 12 is a sectional view taken along the line XII—XII in FIG. 9.
Figure 13:
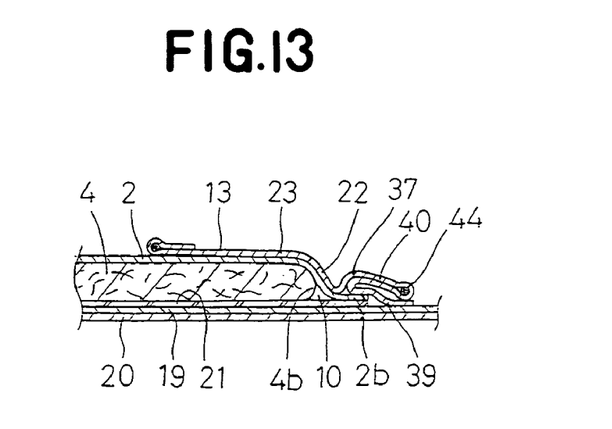
FIG. 13 is a sectional view taken along the line XIII—XIII in FIG. 9.

Referring to FIGS. 12 and 13, the longitudinally opposite ends 40 of the third and fourth barrier flaps 37, 38 lying on the side of the end flaps 9 are permanently bonded to the proximal portions 39 lying on the end flaps 9 (See FIG. 13). Alternatively, an embodiment is also possible without departing from the scope of the invention in which the longitudinally opposite ends 40 of the third and fourth barrier flaps 37, 38 lying on the respective end flaps 9 are permanently bonded to the proximal portions 22 extending in the vicinity of the side edges 10 of the absorbing zone 45 with these ends 23 collapsed inwardly in the transverse direction of the article 1B.

The side flaps 11, 12 principally comprise the backsheet 3 and the barrier flaps 37, 38. In the side flaps 11, 12, the side edges 2b of the topsheet 2 extend outwardly slightly beyond the side edges 4b of the core 4 in the transverse direction and the side edges 3b of the backsheet 3 as well as the proximal portions 39 of the respective barrier flaps 37, 38 extend outwardly beyond the side edges 2b of the topsheet 2.

In the side flaps 11, 12, the side edges 2b, 3b of the top- and backsheets 2, 3, respectively, and the proximal portions 39 of the barrier flaps 37, 38 are overlapped together wherein the proximal portions 39 of the flaps 37, 38 are permanently bonded to the outer surface of the topsheet 2 along its side edges 2b the inner surface of the backsheets 3 along its side edges 3b.

In this article 1B, the first and second sections 33, 34 of the crotch region 6 are tucked inwardly along the first and second folding guide lines 30, 32, respectively, and thereby the transverse dimension of the crotch region 6 in its longitudinal middle zone 28 can be reduced. Thus the absorbing zone 45 of the crotch region 6 is neatly received in the wearer's crotch region as the article 1B is put on the wearer's body and it is unlikely that the core 4 laid in the absorbing zone 45 might enhance the bulkiness of this zone 45 and the article 1B might give the wearer a feeling of discomfort due to the enhanced stiffness. Even when the crotch region 6 is squeezed in the wearer's crotch region, there is no possibility that the absorbing zone 45 might be formed with a plurality of irregular creases and the absorbing function of the zone 45 might be thereby deteriorated.

While the first and second sections 33, 34 of the crotch region 6 are tucked inwardly, the distal portions 24 of the first and second barrier flaps 13, 14 extend almost linearly without being affected by such tucking. There is no anxiety, therefore, that the distal portions 24 might be collapsed toward the body fluid absorbing zone 45. In the case of the diaper 1B, the distal portions 41 of the third and fourth barrier flaps 37, 38 are tucked inwardly together with the first and second sections 33, 34 in the transverse direction and the folded zones of these distal portions 41 come in contact with the distal portions 24 of the barrier flaps 13, 14 from outside and thereby support the distal portions 24 of the barrier flaps 13, 14. In this way, the distal portions 24 of the first and second barrier flaps 13, 14 are reliably prevented from being collapsed outwardly in the transverse direction of the article 1B.

In the article 1B, the distal portions 24 of the first and second barrier flaps 13, 14 rise up in entirety above the absorbing zone 45 and thereby effectively function as the barriers against body fluids. Namely, even if bodily exudates spread in the absorbing zone 45 in the transverse direction, it is unlikely that bodily exudates might flow beyond the distal portions 24 and any sideway leakage of bodily exudates in the crotch region 6 can be reliably prevented. The article 1B is free from an anxiety that the distal edges 26 of the distal portions 24 of the respective barrier flaps 13, 14 might get nearer to each other as the article 1B is put on the wearer's body and consequently bodily exudates might be discharged on outer sides of the barrier flaps 13, 14. Furthermore, the distal portions 24 do not cover the absorbing zone 45, so it is unlikely that the absorbing function desired for the absorbing zone 45 might be restrained by the distal portions. Thus bodily exudates discharged on the article 1B put on the wearer's body can be reliably absorbed by the core 4 through the topsheet 2 and retained therein.

Stock materials for the topsheet 2 may be selected from the group consisting of a hydrophobic fibrous nonwoven fabric having a plurality of apertures and a plastic film having a plurality of fine perforations. Stock materials for the backsheet 3 may be selected from the group consisting of a breathable hydrophobic fibrous nonwoven fabric, a breathable liquid-impervious plastic film and a composite nonwoven fabric comprising two breathable hydrophobic fibrous nonwoven fabric layers laminated one upon another and a composite sheet comprising a hydrophobic fibrous nonwoven fabric and a breathable liquid-impervious plastic film laminated one upon another. As stock materials for the barrier flaps 13, 14, 37, 38, the same materials as that for the backsheet. 3 may be used. The nonwoven fabric may be selected from those obtained by spun lace-, needle punch-, melt blown-, thermal bond-, spun bond- and chemical bond-processes.

As stock materials for the backsheet 3 and the barrier flaps 13, 14, 37, 38, it is also possible to use a composite nonwoven fabric (SM nonwoven fabric or SMS nonwoven fabric) consisting of a melt blown fibrous nonwoven fabric having a high water-resistance and a spun bond fibrous nonwoven fabric having a high strength as well as a high flexibility laminated on at least one side of the melt blown fibrous nonwoven fabric.

The hydrophilic fibrous nonwoven fabric may be made of any one of synthetic fibers, semi-synthetic fibers and regenerated fibers each modified to become hydrophilic or conjugate fibers thereof. The hydrophobic fibrous nonwoven fabric may be formed from synthetic fibers and may contain therein semi-synthetic fibers or regenerated fibers both treated to become water repellent. While not specified, the synthetic fibers may be selected from the group consisting of polyester-, polyacrylonitrile-, polyvinyl chloride-, polyethylene-, polypropylene- and polystyrene-based fibers. The suitably useful synthetic fibers further include core-sheath type conjugate fibers, side-by-side type conjugate fibers, macaroni fibers, microporous fibers and bonded-type conjugate fibers.

Permanent bonding of the top- and backsheets 2, 3 to each other, permanent bonding of the barrier flaps 13, 14, 37, 38 to the top- and backsheets 2, 3, permanent bonding of the core 4 to the top- and backsheets 2, 3 and permanent bonding of the elastic members 27, 35, 36, 44 to the backsheet 3 and the barrier flaps 13, 14, 37, 38 may be achieved using suitable adhesives or welding techniques such as heat-sealing and ultrasonic sealing. As adhesives, hot melt adhesives, acrylic adhesives and elastomeric adhesives. Preferably, the adhesives may be applied on the top- and backsheets 2, 3 and the barrier flaps 13, 14, 37, 38 in a suitable pattern selected from the group consisting of a spiral pattern, a zigzag pattern, a dotted pattern and a striped pattern.

What is claimed is:

1. A pull-on disposable wearing article, comprising:
   a front waist region;
   a rear waist region opposed to said front waist region;
   a crotch region extending in a longitudinal direction of said article between said waist regions;
   a waist-hole;
   a pair of leg-holes;
   an absorbing zone extending between said front and rear waist regions;
   a pair of end flaps extending in a transverse direction of said article and outside longitudinally opposite ends of said absorbing zone;
   first and second side flaps extending in the longitudinal direction and outside transversely opposite side edges of said absorbing zone, respectively;
   first and second barrier flaps extending in the longitudinal direction on said first and second side flaps, respectively, each of said first and second barrier flaps comprising
   a proximal portion extending in the longitudinal direction, longitudinally opposite ends lying on said end flaps and collapsed inwardly in the transverse direction, and
   a distal portion being elastically stretchable and contractible and biased to extend upward from said proximal portion;
   a pair of first folding guide lines extending, in a longitudinally middle zone of said crotch region, from a vicinity of the proximal portion of said first barrier flap toward a side edge of said first side flap and towards said front and rear waist regions, respectively;
   a pair of second folding guide lines extending, in a longitudinally middle zone of said crotch region, from a vicinity of the proximal portion of said second barrier flap toward a side edge of said second side flap and towards said front and rear waist regions, respectively; and
   third and fourth barrier flaps extending in the longitudinal direction outside said first and second barrier flaps, respectively, each of said third and fourth barrier flaps comprising
   a proximal portion extending in the longitudinal direction, longitudinally opposite ends lying on said end flaps and collapsed outwardly in the transverse direction, and
   a distal portion being elastically stretchable and contractible and biased to extend upwardly from said proximal portion;
   wherein
   a first section of said crotch region defined by said first folding guide lines and the side edge of said first side flap is folded along said first folding guide lines and tucked inwardly of said article, and a second section of said crotch region defined by said second folding guide lines and the side edge of said second side flap is folded along said second folding guide lines and tucked inwardly of said article;
   the distal portions of said first and second barrier flaps are not folded and tucked inwardly together with said first and second sections, whereas the distal portions of said third and fourth barrier flaps are folded and tucked inwardly together with said first and second sections.

2. The wearing article according to claim 1, further comprising stretchable elastic members extending in the longitudinal direction and being contractibly attached to the distal portions of said first and second barrier flaps.

3. The wearing article according to claim 2, further comprising stretchable elastic members extending in the longitudinal direction and being contractibly attached to the distal portions of said third and fourth barrier flaps.

4. The wearing article according to claim 1, wherein said article comprises a liquid-pervious topsheet, a liquid-impervious backsheet, and a liquid-absorbent core interposed between said topsheet and backsheet, and wherein said core defines said absorbing zone.

5. The wearing article according to claim 2, wherein said stretchable elastic members bias the distal portions of said third and fourth barrier flaps to extend both upwardly from the respective proximal portions and outwardly away from said absorbing zone.

6. The wearing article according to claim 5, wherein said stretchable elastic members bias the distal portions of said first and second barrier flaps to extend both upwardly from the respective proximal portions and inwardly of said absorbing zone.

7. The wearing article according to claim 1, wherein, at the longitudinally opposite ends of each of said third and fourth barrier flaps, said distal portion is folded outwardly and bonded to said proximal portion.

8. A pull-on disposable wearing article having longitudinal and transverse directions, said article comprising:
   a liquid impervious cover sheet defining front and rear regions and a crotch region extending in the longitudinal direction between said front and rear regions;
   a pad comprising a liquid-pervious topsheet, a liquid-impervious backsheet attached to an upper side of said cover sheet, and a liquid-absorbent core interposed between said topsheet and backsheet; and first and second barrier flaps each having a proximal portion bonded to the topsheet of said pad, a distal portion, and an elastic member attached to said distal portion to bias said distal portion to extend upward from said topsheet of said pad and outwardly in the transverse direction away from said pad;

wherein transversely opposite lateral portions of the crotch region are folded along a pair of V-shaped folding lines and tucked inwardly of the article;

wherein the article further comprises third and fourth barrier flaps each having a proximal portion bonded to the topsheet of said pad, a distal portion, and an elastic member attached to said distal portion to bias said distal portion to extend upward from said topsheet of said pad and inwardly of said pad in the transverse direction; and wherein the distal portions of said third and fourth barrier flaps are not folded and tucked together with the transversely opposite lateral portions of the crotch region, whereas the distal portions of said first and second barrier flaps are folded and tucked together with the transversely opposite lateral portions of the crotch region.

9. The article according to claim 8, wherein each of said first and second barrier flaps comprises a material layer having a first section which is bonded to at least one of the topsheet of said pad and the upperside of said cover sheet to define said proximal portion, and a second section which is continuous to said first section and free of direct attachment to said topsheet of said pad at least in said crotch region to define said distal portion;

wherein at longitudinally opposite ends of each of said first and second barrier flaps, the second section is folded over the first section, outwardly in the transverse direction, and bonded to the said first section.

10. The article according to claim 9, wherein the material layer of each of said first and second barrier flaps further has a third section which is continuous to said second section and bonded to the topsheet of said pad to define the proximal portion of one of said third and fourth barrier flaps, respectively; and a fourth section which is continuous to said third section and free of direct attachment to said topsheet of said pad at least in said crotch region to define the distal portion of said one of said third and fourth barrier flaps, respectively;

wherein at longitudinally opposite ends of each of said third and fourth barrier flaps, the fourth section is folded over the third section, inwardly of said pad in the transverse direction, and bonded to the said third section.

* * * * *